(12) United States Patent
Vaughn et al.

(10) Patent No.: US 6,444,868 B1
(45) Date of Patent: Sep. 3, 2002

(54) PROCESS TO CONTROL CONVERSION OF $C_{4+}$ AND HEAVIER STREAM TO LIGHTER PRODUCTS IN OXYGENATE CONVERSION REACTIONS

(75) Inventors: Stephen N. Vaughn, Kingwood; Peter G. Ham, Houston; Keith H. Kuechler, Friendswood, all of TX (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/521,175

(22) Filed: Mar. 8, 2000

Related U.S. Application Data

(63) Continuation-in-part of application No. 09/251,142, filed on Feb. 17, 1999.

(51) Int. Cl.[7] .............................................. C07C 1/207
(52) U.S. Cl. ..................... 585/640; 585/311; 585/312; 585/313; 585/324; 585/638; 585/639
(58) Field of Search .................. 585/311, 312, 585/313, 324, 638, 634, 640

(56) References Cited

U.S. PATENT DOCUMENTS

| | | | |
|---|---|---|---|
| 2,388,929 A | 11/1945 | Mottern | 260/682 |
| 3,221,073 A | 11/1965 | Davis et al. | 260/677 |
| 4,058,576 A | 11/1977 | Chang et al. | 260/673 |
| 4,071,573 A | 1/1978 | Owen et al. | 260/668 R |

(List continued on next page.)

FOREIGN PATENT DOCUMENTS

| | | |
|---|---|---|
| CA | 1 130 820 | 8/1982 |
| CA | 1 196 031 | 10/1985 |
| EP | 088 494 | 9/1983 |
| EP | 091 751 | 10/1983 |
| EP | 359841 | * 3/1990 |
| EP | 0642485 | 3/1995 |
| EP | 882 692 | 12/1998 |
| WO | WO97/36845 | 10/1997 |
| WO | WO99/15482 | 4/1999 |

OTHER PUBLICATIONS

"MTO—has its time come!"Nitrogen & Methanol, No. 246, Jul.–Aug. 2000.
Barger et al., "Converting Natural Gas to Ethylene and Proplene by the UOP/Hydro MTO Process," 12th International Zeolite Conference 1999 Materials Research Society p. 567–573.
Chang, "Methanol Conversion to Light Olefins," Catal. Rev.–Sci. Eng., 26(3&4), 323–345 (1984).
Kaeding et al., "Production of Chemicals from Methanol," Journal of Catalysis 61, 155–164 (1980).
Liang et al., "Characteristics and Performance of SAPO–34 Catalyst for Methanol–to–Olefin Conversion," Applied Catalysis, 64 (1990) 31–40.
Marchi et al., "Catalytic Conversion of Methanol to Light Alkenes on SAPO Molecular Sieves," Applied Catalysis, 71 (1991) 139–152.

Primary Examiner—Thuan D. Dang
(74) Attorney, Agent, or Firm—Paul T. LaVoie

(57) ABSTRACT

A method for converting heavy olefins present in a product stream exiting a first reaction zone into light olefins and carbonaceous deposits on a catalyst without separation of the heavy olefins from the product stream exiting the first reaction zone. The method comprises creating the product stream exiting the first reaction zone, the product stream exiting the first reaction zone comprising the heavy olefins, moving the product stream exiting the first reaction zone to a second reaction zone without separation of the heavy olefins from the product stream exiting the first reaction zone, and contacting the product stream exiting the first reaction zone with the catalyst under conditions effective to form the light olefins, the contacting causing the carbonaceous deposits to form on at least a portion of the catalyst.

18 Claims, 1 Drawing Sheet

U.S. PATENT DOCUMENTS

| | | | |
|---|---|---|---|
| 4,072,732 A | 2/1978 | Hargis et al. | 260/682 |
| 4,072,733 A | 2/1978 | Hargis et al. | 260/682 |
| 4,083,888 A | 4/1978 | Caesar et al. | 200/682 |
| 4,083,889 A | 4/1978 | Caesar et al. | 260/682 |
| 4,138,440 A | 2/1979 | Chang et al. | 260/668 |
| 4,163,721 A | 8/1979 | Lobdell | 210/232 |
| 4,229,608 A * | 10/1980 | Chen et al. | 585/640 |
| 4,328,384 A | 5/1982 | Daviduk et al. | 585/469 |
| 4,338,475 A | 7/1982 | Pennington et al. | 585/408 |
| 4,379,123 A | 4/1983 | Daviduk et al. | 422/142 |
| 4,396,789 A | 8/1983 | Barrocas | 585/639 |
| 4,423,274 A | 12/1983 | Daviduk et al. | 585/640 |
| 4,431,856 A | 2/1984 | Daviduk et al. | 585/469 |
| 4,433,188 A | 2/1984 | Hoelderich et al. | 585/640 |
| 4,440,871 A | 4/1984 | Lok et al. | 502/214 |
| 4,449,961 A | 5/1984 | Forbus et al. | 585/640 |
| 4,499,327 A | 2/1985 | Kaiser | 585/640 |
| 4,547,616 A | 10/1985 | Avidan et al. | 585/640 |
| 4,560,537 A | 12/1985 | Tabak | 422/190 |
| 4,579,999 A | 4/1986 | Gould et al. | 585/312 |
| 4,590,320 A | 5/1986 | Sapre | 585/324 |
| 4,665,268 A | 5/1987 | Lee et al. | 585/640 |
| 4,677,242 A | 6/1987 | Kaiser | 585/638 |
| 4,677,243 A | 6/1987 | Kaiser | 585/638 |
| 4,689,205 A | 8/1987 | Gould et al. | 422/142 |
| 4,752,651 A | 6/1988 | Kaiser | 585/640 |
| 4,861,938 A | 8/1989 | Lewis et al. | 585/640 |
| 4,873,390 A | 10/1989 | Lewis et al. | 585/638 |
| 4,899,002 A | 2/1990 | Harandi et al. | 585/312 |
| 4,912,281 A | 3/1990 | Wu | 585/640 |
| 4,973,792 A | 11/1990 | Lewis et al. | 585/638 |
| 5,028,400 A | 7/1991 | Harandi et al. | 422/211 |
| 5,045,287 A | 9/1991 | Harandi et al. | 422/142 |
| 5,059,738 A | 10/1991 | Beech, Jr. et al. | 585/469 |
| 5,095,163 A | 3/1992 | Barger | 585/640 |
| 5,126,308 A | 6/1992 | Barger et al. | 502/214 |
| 5,157,181 A | 10/1992 | Stine et al. | 585/329 |
| 5,177,283 A | 1/1993 | Ward | 585/446 |
| 5,191,141 A | 3/1993 | Barger et al. | 585/640 |
| 5,278,345 A | 1/1994 | Janssen et al. | 585/640 |
| 5,414,181 A | 5/1995 | Bearden, Jr. et al. | 585/654 |
| 5,447,622 A | 9/1995 | Kerby et al. | 208/78 |
| 5,475,182 A | 12/1995 | Janssen | 585/640 |
| 5,510,559 A | 4/1996 | Barger et al. | 585/664 |
| 5,714,662 A | 2/1998 | Vora et al. | 585/640 |
| 5,714,663 A | 2/1998 | Serrand et al. | 585/648 |
| 5,744,680 A | 4/1998 | Mulvaney, III et al. | 585/640 |
| 5,811,621 A | 9/1998 | Van Dijk | 585/639 |
| 5,817,906 A | 10/1998 | Marker et al. | 585/640 |
| 5,904,880 A | 5/1999 | Sun | 252/373 |
| 5,907,076 A | 5/1999 | Ou et al. | 585/800 |
| 5,912,393 A | 6/1999 | Barger et al. | 585/640 |
| 5,914,433 A | 6/1999 | Marker | 585/313 |
| 5,925,586 A | 7/1999 | Sun | 502/62 |
| 5,925,800 A | 7/1999 | Sun et al. | 585/640 |
| 5,927,063 A | 7/1999 | Janda et al. | 60/39.02 |
| 5,932,512 A | 8/1999 | Sun | 502/214 |
| 5,952,538 A | 9/1999 | Vaughn et al. | 585/640 |
| 5,960,643 A | 10/1999 | Kuechler et al. | 62/620 |
| 5,962,762 A | 10/1999 | Sun et al. | 585/640 |
| 5,972,203 A | 10/1999 | Smith et al. | 208/113 |
| 6,004,898 A | 12/1999 | Sun | 502/214 |
| 6,005,155 A | 12/1999 | Sun | 585/640 |
| 6,023,005 A | 2/2000 | Lattner et al. | 585/639 |
| 6,040,257 A | 3/2000 | Drake et al. | 502/64 |
| 6,040,264 A | 3/2000 | Sun et al. | 502/214 |
| 6,046,371 A | 4/2000 | Wu et al. | 585/638 |
| 6,046,373 A | 4/2000 | Sun | 585/640 |
| 6,051,745 A | 4/2000 | Wu et al. | 585/638 |
| 6,051,746 A | 4/2000 | Sun et al. | 585/638 |
| 6,057,261 A | 5/2000 | Sun | 502/341 |
| 6,166,282 A | 12/2000 | Miller | 585/638 |

\* cited by examiner

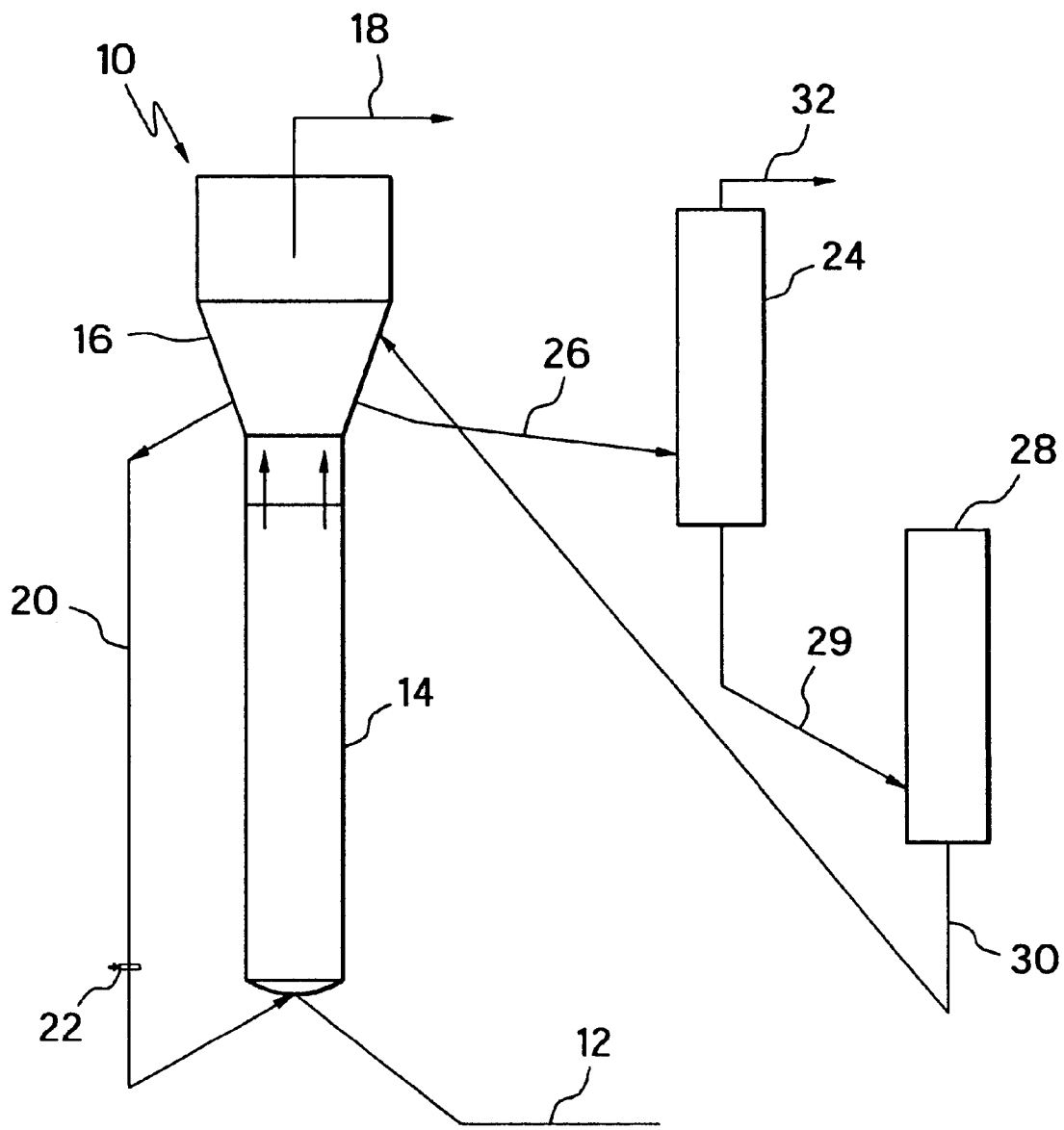

PROCESS TO CONTROL CONVERSION OF $C_4^+$ AND HEAVIER STREAM TO LIGHTER PRODUCTS IN OXYGENATE CONVERSION REACTIONS

RELATED APPLICATIONS

This application is a continuation-in-part of application Ser. No. 09/251,142 filed Feb. 17, 1999, entitled "OXYGENATE CONVERSION REACTIONS," the entire disclosure of which is hereby incorporated herein by reference.

FIELD OF THE INVENTION

The present invention relates to a method for increasing the selectivity to light olefins and/or for decreasing $C_4^+$ formation in oxygenate conversion reactions.

BACKGROUND OF THE INVENTION

Light olefins, defined herein as ethylene, propylene, and mixtures thereof, serve as feedstocks for the production of numerous important chemicals and polymers. Heavy olefins are defined herein as the hydrocarbon products heavier than light olefins. Light olefins traditionally are produced by cracking petroleum feeds. Because of the limited supply of competitive petroleum feeds, the opportunities to produce low cost light olefins from petroleum feeds are limited. Efforts to develop light olefin production technologies, based on alternative feedstocks have increased.

Important types of alternate feedstocks for the production of light olefins are oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The reaction, which converts oxygenates to desired light olefins, also produces by-products. Representative by-products include, for example, alkanes (methane, ethane, propane, and larger), $C_4^+$ olefins, aromatic compounds, carbon oxides and carbonaceous deposits (also referred to as "coke").

During the conversion of oxygenates to light olefins, carbonaceous deposits accumulate on the catalysts used to promote the conversion reaction. As the amount of these carbonaceous deposits increases, the catalyst begins to lose activity and, consequently, less of the feedstock is converted to the light olefin products. At some point, the build up of these carbonaceous deposits causes the catalyst to reduce its capability to convert the oxygenates to light olefins. When a catalyst can no longer convert oxygenates to olefin products, the catalyst is considered to be deactivated. Once a catalyst becomes deactivated, it must be removed from the reaction vessel and replaced with fresh catalyst. Such complete replacement of the deactivated catalyst is expensive and time consuming. To reduce catalyst costs, the carbonaceous deposits are periodically fully or partially removed from the deactivated and/or partially deactivated catalyst to allow for reuse of the catalyst. Removal of the deactivated catalyst and/or partially deactivated catalyst from the reaction process stream to remove the carbonaceous deposits is typically referred to as regeneration and is typically conducted in a unit called a regenerator.

Previously in the art, catalyst regeneration was accomplished by removing the deactivated catalyst from the process stream, removing the carbonaceous deposits from the catalyst, and then returning the regenerated catalyst to the reactor near the inlet of the reactor or reaction vessel. Conventionally, this inlet is located near the bottom quarter of the reactor or reaction vessel. By returning the regenerated catalyst near the inlet of the reactor, the regenerated catalyst would immediately contact fresh feedstock and begin conversion of the feedstock. However, doing so does nothing to control the conversion of the feedstock into by-products.

For example, U.S. Pat. No. 4,873,390 to Lewis et al. teaches a process for catalytically converting a feedstock into a product in which the feedstock is contacted with a partially regenerated catalyst. Lewis et al. describes that a partially regenerated catalyst improves the selectivity of the process to the light olefin products. While contacting the feedstock with a partially regenerated catalyst may improve the selectivity of the process to the light olefin products, it does nothing to control production of by-products.

For these reasons, a need exists in the art for improved processes which increase light olefin selectivity and control production of by-products.

SUMMARY OF THE INVENTION

The present invention solves the current needs in the art by providing a method for increasing light olefin production and controlling production of by-products.

One aspect of the present invention is directed to a method for selectivating a catalyst. As used herein, the word "selectivate" (or selectivating) refers to a process by which a certain amount of carbonaceous deposits are formed on the catalyst to cause the catalyst to produce more ethylene and propylene from the oxygenate feed and to produce fewer by-products. In the present invention, the selectivation of the catalyst occurs by contacting the catalyst with the by-products of the conversion reaction. However, the light olefins produced by the oxygenate conversion reaction can also be used for the selectivation of the catalyst, either separately or in combination with the by-products. As one well skilled in the art will appreciate, it is preferred that as much as possible of the by-products selectivate the catalyst and as little as possible of the light olefins selectivate the catalyst. As the by-products contact an at least partially regenerated catalyst, primarily the $C_4^+$ olefin portion of the by-products, is primarily converted to light olefins and carbonaceous deposits which form on the catalyst. While the accumulation of the carbonaceous deposits does contribute to the deactivation of the catalyst, the accumulation of the carbonaceous deposits also contributes to the selectivation of the catalyst. When the selectivated catalyst mixture then contacts the oxygenate feed, selectivity of the conversion reaction to forming light olefins, particularly ethylene and propylene, is increased and/or formation of by-products is reduced compared to using a fresh or regenerated catalyst that has not been selectivated according to the present invention.

The method for selectivating the catalyst comprises contacting, in a reactor, a feedstock, including oxygenates, with a molecular sieve catalyst under conditions effective to form a product including light olefins and by-products, the contacting causing carbonaceous deposits to form on at least a portion of the molecular sieve catalyst producing deactivated catalyst; removing a portion of the deactivated catalyst from the reactor; regenerating the portion of the deactivated catalyst to remove at least a portion of the carbonaceous deposits from the deactivated catalyst removed from the reactor to form an at least partially regenerated catalyst; and exposing at least a portion of the at least partially regenerated catalyst to at least a portion of the by-products to selectivate the at least partially regenerated catalyst to form light olefins. In this process, the at least partially regenerated catalyst may also be exposed to at least a portion of the light olefins to selectivate the at least partially regenerated catalyst to forming light olefins. This process may also include the step of contacting at least a portion of the selectivated at least partially regenerated catalyst with the feedstock.

Another aspect of the present invention is directed to a method for converting oxygenates to light olefins. The method comprises contacting, in a reactor, a feedstock comprising oxygenates with a molecular sieve catalyst under conditions effective to convert the feedstock to a product including light olefins and by-products, the contacting causing carbonaceous deposits to form on at least a portion of the molecular sieve catalyst producing deactivated catalyst; removing a portion of the deactivated catalyst from the reactor; regenerating the portion of the deactivated catalyst under conditions effective to remove at least a portion of the carbonaceous deposits from the deactivated catalyst to form an at least partially regenerated catalyst; exposing at least a portion of the at least partially regenerated catalyst to at least a portion of the by-products to selectivate the portion of the at least partially regenerated catalyst to form light olefins; and contacting the selectivated portion of the at least partially regenerated catalyst with the feedstock to form the product. In this method, the at least partially regenerated catalyst may also be is exposed to at least a portion of the light olefins to selectivate the at least partially regenerated catalyst to forming light olefins. This method may include the additional step of recovering the light olefins. If the light olefins are recovered, then this method may also include the step of polymerizing the light olefins to form polyolefins.

Still another aspect of the present invention is directed to a method for reducing the heat of reaction in a reactor by offsetting the exothermic conversion of a feedstock during a catalyzed chemical conversion process. The method comprises contacting, in a reactor, a feedstock with a catalyst under conditions effective to form a product and by-products, the contacting causing carbonaceous deposits to form on at least a portion of the catalyst causing at least a portion of the catalyst to become deactivated catalyst; removing at least a portion the deactivated catalyst from the reactor; regenerating the portion of the deactivated catalyst removed from the reactor to remove at least a portion of the carbonaceous deposits from the deactivated catalyst to form an at least partially regenerated catalyst; and contacting the at least partially regenerated catalyst with the by-products to facilitate an endothermic reaction with the by-products.

Yet another aspect of this invention provides a method for converting heavy olefins present in a product stream into light olefins and carbonaceous deposits on a catalyst without separation of the heavy olefins from the product stream exiting the first reaction zone. The method comprises the following steps: producing a product stream in a first reaction zone, the product stream including heavy olefins; moving the product stream from the first reaction zone to a second reaction zone without separation of the heavy olefins from the product stream; and contacting the product stream with a catalyst in the second reaction zone under conditions effective to form the light olefins, the contacting causing carbonaceous deposits to form on at least a portion of the catalyst producing a deactivated catalyst.

Another aspect of this invention provides a method for controlling the conversion of heavy olefins into light olefins. This method comprises the following steps: creating a first product stream in a first reaction zone, the first product stream comprising heavy olefins; moving the first product stream to a second reaction zone; and contacting the first product stream with a catalyst present in the second reaction zone under conditions effective to form a second product stream comprising the light olefins, the contacting causing carbonaceous deposits to form on at least a portion of the catalyst producing a deactivated catalyst, wherein the amount of the catalyst in the second reaction zone is controlled by a mechanism. The first product stream can be the same or different from the product stream exiting the first reaction zone.

Other advantages and uses of the process of the present invention will become apparent from the following detailed description and appended drawing and claims.

BRIEF DESCRIPTION OF THE DRAWING

The FIGURE shows a reactor useful to conduct the processes of the present invention.

DETAILED DESCRIPTION OF THE INVENTION

When converting oxygenates to light olefins, it is desirable to maximize the production of light olefins, and to control, typically to minimize, the production of by-products. This invention accomplishes this result by contacting a fresh, fully regenerated, or partially regenerated catalyst with an olefin product stream containing a substantial quantity of heavier hydrocarbon by products, i.e., $C_4^+$ hydrocarbons, particularly $C_4^+$ olefins. After contacting, the same catalyst is used to contact an oxygenate stream containing at least 50 wt. % oxygenate. This manner of contacting a catalyst with a stream containing a substantial quantity of $C_4^+$ hydrocarbon by product, and then a stream rich in oxygenate, provides a product rich in light olefins.

The process of the present invention for converting oxygenates to light olefins employs an organic starting material (feedstock) desirably comprising oxygenates. As used herein, the term "oxygenates" is defined to include, but is not necessarily limited to, aliphatic alcohols, ethers, carbonyl compounds (aldehydes, ketones, carboxylic acids, carbonates, and the like), alkyl halides and mixtures thereof. The aliphatic moiety desirably should contain in the range of from about 1–10 carbon atoms and more desirably in the range of from about 1–4 carbon atoms. Representative oxygenates include, but are not necessarily limited to, lower straight chain or branched aliphatic alcohols, their unsaturated counterparts, and their halogen analogues. Examples of suitable compounds include, but are not necessarily limited to, the following: methanol; ethanol; n-propanol; isopropanol; $C_4$–$C_{10}$ alcohols; methyl ethyl ether; dimethyl ether; diethyl ether; di-isopropyl ether; methyl formate; methyl chloride, methyl bromide, methyl iodide, ethyl chloride; ethyl bromide, ethyl iodide, formaldehyde; di-methyl carbonate; methyl ethyl carbonate, acetone; n-alkyl halides having n-alkyl groups of comprising the range of from about 3 to about 10 carbon atoms; and mixtures thereof. Desirably, the oxygenate used in the conversion reaction are methanol, dimethyl ether and mixtures thereof. More desirably the oxygenate is methanol. As used herein, the term "oxygenate" designates only the organic material used as the feed. The total charge of feedstock to the reaction zone may contain additional compounds, such as diluents.

In the present invention, an oxygenate feed is contacted in a first reaction zone of a reactor with a molecular sieve catalyst at process conditions effective to produce light olefins, i.e., an effective temperature, pressure, WHSV and, optionally, an effective amount of diluent, correlated to produce light olefins. The light olefin-containing product generally contains undesirable by-products such as heavier olefins, which are typically removed before further processing. In this invention, however, the heavier olefins need not be removed from the light olefin-containing product. Instead, this product can be used as a feed material and the feed can be brought to a second reaction zone for additional contact with molecular sieve catalyst. In this additional reaction zone, heavier olefins also contained in the product are converted to light olefins. Under the appropriate conditions, the heavier olefins are converted relatively quickly to light olefins compared to any further reactions in which the light olefins originally present in the feed might undergo. Such conditions are further discussed below.

Usually, the oxygenate feed is contacted with the catalyst when the oxygenates are in a vapor phase. Alternately, the process may be carried out in a liquid or a mixed vapor/liquid phase. When the process is carried out in a liquid phase or a mixed vapor/liquid phase, different conversions and selectivities of feedstock-to-product may result depending upon the catalyst and reaction conditions.

In a reactor operating at steady state or a semi-steady state conditions, a mixture of a partially deactivated catalyst fraction, a deactivated catalyst fraction and a partially or fully regenerated catalyst fraction are typically present in the first and second reaction zones. In order to form a desired catalyst mixture, at least a portion of the deactivated catalyst from the first reaction zone is desirably removed and sent to a regenerator. In the regenerator, carbonaceous (i.e., coke) deposits are removed from the catalyst. Desirably, the catalyst is regenerated to have an average level of coke effective for selectively converting $C_4^+$ olefins to ethylene and/or propylene. Desirably, the catalyst will be regenerated such that the regenerated catalyst will have a coke content of less than 5 wt. %, desirably less than 2 wt. %, and more desirably less than 1.0 wt. %.

Desirably, a portion of the deactivated catalyst remains in the reactor, and a portion of catalyst is removed from the reactor for regeneration and recirculation back to the reactor. Desirably catalyst removal is at a rate of from about 0.1 times to about 10 times, more desirably from about 0.2 times to about 5 times, and most desirably from about 0.3 to about 3 times the total feed rate of oxygenates to the reactor.

It has been found in the present invention that the use of a fresh, fully regenerated, or partially regenerated catalyst in selectively converting $C_4^+$ hydrocarbons provides better overall light olefin selectivity with reasonable catalyst activity, and provides better control of the reaction temperature inside of the reactor than prior art processes. The regeneration temperature in the catalyst regenerator measures from about 250° C. to about 750° C. and desirably from about 300° C. to about 700° C. Desirably, the catalyst regenerator includes a catalyst separator, desirably a plurality of cyclones, to separate flue gases from the catalyst.

Regeneration is carried out in the presence of a gas comprising oxygen or other oxidants. Examples of other oxidants include, but are not necessarily limited to, singlet $O_2$, $O_3$, $SO_3$, $N_2O$, NO, $NO_2$, $N_2O_5$, and mixtures thereof. Air and air diluted with steam, nitrogen and/or $CO_2$ are desired regeneration gases. Desirably, the oxygen concentration in the regenerator is reduced to a controlled level to minimize overheating or the creation of hot spots in the spent or deactivated catalyst. The deactivated catalyst may also be regenerated reductively with hydrogen, carbon monoxide, mixtures of hydrogen and carbon monoxide, or other suitable reducing agents and gases. Depending on the other oxygenate conversion reaction parameters and the feedstock, a combination of an oxidative regeneration and a reductive regeneration can be employed.

Before the deactivated catalyst is regenerated, especially oxidatively regenerated, at least some of the volatile organics are desirably stripped from the catalyst in a stripper or stripping chamber, using steam, nitrogen, or methane, among others. Stripping the catalyst may improve the process economics, process operation and/or emission control. If the organics are not removed, they will provide at most fuel value. With removal, the recovered organics may have a higher value as chemicals, not as fuels. In addition, the amount of organics removed during regeneration or partial regeneration is reduced. This leads to better heat management both in the catalyst regenerator and on the catalyst, particularly when an oxidative regeneration method is used. Less carbon oxides are generated in an oxidative regeneration mode because there are less organics to be oxidatively removed.

After being regenerated, and optionally stripped, the catalyst is exposed to the product stream from the first reaction zone. This contact with the product stream occurs in the second reaction zone of the reactor.

The product stream that flows into the second reaction zone will typically contain a significant portion of $C_4^+$ hydrocarbons along with the desirable light olefin products. The inventors have found that contacting this stream with fresh or regenerated catalyst selectively converts the $C_4^+$ hydrocarbons in the product stream to additional light olefins. This means that a significant portion the $C_4^+$ hydrocarbons are converted to light olefins relative to the light olefin compositions already present in the stream being further reacted into undesirable by-product.

Desirably the product stream that enters the second reaction zone will comprise at least 50 wt. % light olefin (i.e., a combination of ethylene and propylene), desirably at least 55 wt. % light olefin, more desirably at least 60 wt. % light olefin. It is also desirable that the product stream have less than 50 wt. % $C_4^+$ hydrocarbons, desirably less than 40 wt. % $C_4^+$ hydrocarbons, more desirably less than 30 wt. % $C_4^+$, and most desirably less than 20 wt. % $C_4^+$ hydrocarbons. It is preferred that the product stream contact the catalyst in the second reaction zone without prior separation of the light olefin components. However, at least a portion of, or substantially all of, the light olefin compounds can be separated if desired. In such a case when prior separation of at least a portion of the light olefin compounds is included, it is desirable to obtain a stream for contacting catalyst in the second reaction zone which has a $C_4^+$ hydrocarbon concentration of at least about 25 wt. % $C_4^+$ hydrocarbons, desirably at least about 30 wt. % $C_4^+$ hydrocarbons, more desirably at least about 40 wt. % $C_4^+$ hydrocarbons, and most desirably at least about 50 wt. % $C_4^+$ hydrocarbons.

The second reaction zone can be located inside of a common reactor vessel along with the first reaction zone, or the second reaction zone and the first reaction zone can be located in separate reactor vessels within the same reactor. Desirably, although not necessarily, the second reaction zone is adjacent to the first reaction zone. Fresh catalyst can also be mixed with the regenerated catalyst as desired.

The second reaction zone can also contain a portion of catalyst that has been transferred to the second reaction zone along with the product from the first reaction zone. Desirably this combination of fresh catalyst, catalyst from the regenerator, and catalyst from the first reaction zone will contain an average coke content of less than about 40 wt. %, desirably less than about 30 wt. %. It is preferred that the average coke content be in the range of between about 2 and 30 wt. %.

After the fresh or regenerated catalyst has contacted the $C_4^+$ hydrocarbons in the second reaction zone, the catalyst in the second reaction zone is then desirably passed to the first reaction zone to contact the oxygenate stream. Desirably, this contact occurs in counter-current fashion such that the catalyst from the second reaction zone is input at a first end of the first reaction zone and the oxygenate feed is input into a second end of the first reaction zone. If desired, additional fresh or regenerated catalyst can be input to the first reaction zone. The fresh or regenerated catalyst can be input at any point along the first reaction zone. Desirably, fresh or regenerated catalyst is added to the first reaction zone at the same end as the oxygenate stream.

Desirably, the regenerated catalyst is returned to contact the product stream from the first reaction zone while the catalyst is hot. By "hot" it is meant that at least the catalyst from the regenerator is not cooled substantially below the temperature of the catalyst already in the first reaction zone prior to being contacted. For example, catalyst being returned from the regenerator will have a temperature of from about 250° C. to about 750° C. One skilled in the art will appreciate that a slight amount of cooling may take place as the catalyst is transferred from the regenerator to the reactor. Hot catalyst can be used because the regenerated catalyst is not initially contacting the full amount of the oxygenated feedstock but instead the products of the converted feed and higher temperatures can be used to facilitate conversion of the $C_4^+$ hydrocarbons. One skilled in the art will appreciate that the regenerated catalyst will contact some unconverted feed but will not contact enough of he pure feed to reduce the beneficial effects of contacting the regenerated catalyst with product stream from the first reaction zone.

The invention is desirably conducted in a fluidized bed reactor which has a riser region as the first reaction zone and a dense bed region positioned above, or after, the riser region as the second reaction zone. In this preferred embodiment, the regenerated or fresh catalyst can be input: above the dense bed region; immediately below the dense bed region; or anywhere between about the top one fourth of the riser region and the dense bed region. Generally, it is desirable that the catalyst is input between about the top one-fourth of the riser region and about the bottom one fourth of the dense bed region.

The riser region is a section of the reactor in which the catalyst solids substantially move through the reactor axially with the reactant gases (i.e. the oxygenate feed and any diluent). This type of flow regime is achieved by appropriate selection of reaction conditions, including, among others, gas superficial velocity, catalyst particle size and catalyst density. Manipulation of these variables is well known to those skilled in the art. Desirably, the riser region is operated in a fast fluid bed regime or pneumatic conveying regime, and, more desirably, in a fast fluid bed regime.

The dense bed region is a section of the reactor in which the catalyst solids do not substantially move axially through the reactor with the reactant gases, but rather mix randomly within the region. This flow regime is achieved by appropriate selection of reaction conditions, including, among others, gas superficial velocity, catalyst particle size and catalyst density. Manipulation of these variables is well known to those skilled in the art. Desirably, the dense bed region is operated in a bubble-free regime, bubbling regime, slugging or turbulent fluidization regimes. More desirably, the dense bed region is operated in a bubbling, slugging or turbulent fluidization regimes and, most preferably, in a turbulent fluidization regime.

A reactor 10 useful for conducting the process of the present invention is shown in the FIGURE. The reactor 10 includes a first reaction zone 14 and a second reaction zone 16. The first reaction zone 14 adjoins the second reaction zone 16 and the second reaction zone 16 is desirably positioned above the first reaction zone 14. Feed is provided to the reactor 10 through a feed line 12. One skilled in the art will appreciate that, although feed line 12 is shown as connecting with reactor 10 near its bottom, feed can be provided to reactor 10 at various points along reactor 10. The products of the reactor 10 are removed from the reactor 10 through a line 18. At least one catalyst return line 20 returns catalyst from the second reaction zone 16 to the first reaction zone 14. A flow control device 22 is positioned on the catalyst return line 20 to control the flow of catalyst through catalyst return line 20.

With continuing reference to the figure, catalyst is transferred to a stripper 24 through a transfer line 26. Stripped catalyst from the stripper 24 is transferred to a regenerator 28 through a line 29. Effluent from the stripper is removed through a line 32. A line 30 returns catalyst from the regenerator 28 to the reactor 10.

The processes of the present invention can be conducted in the reactor 10. As shown in the Figure, an oxygenate feed is fed to a reactor 10 through a feed line 12. The feed is reacted with a catalyst in a first reaction zone 14 achieving desirably >80% conversion, more desirably >90% conversion and most desirably >99% conversion to products comprising light olefins and heavy olefins as well as small amounts of other products. The first reaction zone 14 operates as a riser region. Subsequently, the product stream of the first reaction zone 14 is passed through a second reaction zone 16, which operates as a dense bed region. In the second reaction zone 16, the heavy olefins are preferentially converted to other products relative to the rate of conversion of the light olefins. The products are removed from the reactor 10 through line 18. By carrying out a second reaction, the amount of heavy olefins present in the product stream can be depleted relative to the depletion of the light olefins, achieving desirably >80% conversion, more desirably >90% conversion and most desirably >99% conversion to products comprising light olefins and heavy olefins as well as small amounts of other products.

An aspect of this invention is to provide a method for converting the heavy olefins present in the product stream exiting the first reaction zone 14 into light olefins and carbonaceous deposits on the catalyst without separating the heavy olefins from the product stream exiting the first reaction zone 14.

Another aspect of this invention is to control the extent of the catalytic reactions in the first reaction zone 14 and the second reaction zone 16. This control of the extent of catalytic reactions can be achieved by controlling the amount of catalyst in the first reaction zone 14 and the second reaction zone 16. In turn, the amount of catalyst in these zones can be controlled by one or more of the following methods: (1) controlling is the rate of recirculation of catalyst in the first reaction zone 14, through the use of a flow control device, such as, for example, flow control device 22; (2) controlling the rate of transport gas flow; and/or (3) controlling the dimension of the catalyst return line(s) 20. Using these methods and other methods known to persons of ordinary skill in the art, the second 20 reaction zone 16, having a controlled size, can be established after the first reaction zone 14.

The second reaction zone 16 is designed to further convert the products exiting the first reaction zone 14, especially the heavy olefins into lighter products and coke, i.e. carbonaceous deposits, with a corresponding decrease in the amount of the heavy olefins remaining in the product stream which exits the reactor through line 18. By varying the amount of catalyst present in the second reaction zone 16, the extent of the second conversion can be controlled. Conversion of the heavy olefins in the second reaction zone 16 can be controlled by the following methods: (1) adjusting the height of the dense bed in the second reaction zone 16; (2) adjusting the temperature of the catalyst in the second reaction zone 16 as compared to the temperature of the catalyst in the first reaction zone 14; (3) controlling the dimensions of the second reaction zone 16; and (4) controlling the amount of carbonaceous deposits on the catalyst present in the second reaction zone 16. Using these illustrative methods and other techniques well known to persons of ordinary skill in the art, the conversion of heavy olefins into lighter products can be controlled in the second reaction zone 16.

Desirably, the mechanism for controlling the amount of the catalyst in the second reaction zone 16 is selected from the group consisting of (1) controlling the height of the riser region in the first reaction zone 14; (2) controlling the height of the dense bed region in the second reaction zone 16; (3) controlling the rate of flow of a transport gas flowing through the dense bed region in the second reaction zone 16; (4) controlling the rate of recirculation of a portion of a catalyst from the top of the riser region to the bottom of the riser region in the first reaction zone 14; (5) adjusting the temperature of the catalyst in the second reaction zone 16; (6) controlling the shape of the dense fluid bed section of the second reaction zone 16; and (7) controlling the amount of deactivated catalyst in the dense bed region of the second reaction zone 16.

Desirably, the temperature of the second reaction zone 16 is higher than the temperature of the first reaction zone 14. Desirably, the temperature in the second reaction zone 16 is at least about 10° C. higher than in the first reaction zone 14, more desirably at least 20° C. higher, and most desirably at least about 25° C. higher.

Second reaction zone 16 desirably has a diameter greater than that of first reaction zone 14. This greater diameter causes the velocity of the reactants, products and catalyst to decrease in the second reaction zone 16. This decrease in velocity results in an increase of the packing density of the catalyst in the second reaction 16. As such, more catalyst is retained in the second reaction zone 16 than in the first reaction zone 14. Therefore, the olefins are thoroughly brought in contact with the catalyst, desirably by a percolation type flow of the olefins through the bed of catalyst in the second reaction zone 16. As a result, the heavy olefins are more deeply depleted and converted to the lighter products in the second reaction zone 16 than in the first reaction zone 14. More desirably, second reaction 16 has the shape of an inverted frustum of a right cone tapering outward from the first reaction zone 14 as shown in the FIGURE. With this shape, the velocity of a carrier gas of a fluidized bed in second reaction zone 16 decreases as the cross-sectional area of the second reaction zone 16 increases. This, in turn, causes the packing density of the catalyst in the second reaction zone 16 to increase in the inverted frustum shaped second reaction zone 16.

An especially useful optional mode of operation comprises recirculating catalyst from the second reaction zone 16 through line 26 to the catalyst stripper 24, in which volatile organic materials are stripped off of the catalyst, and then to the catalyst regenerator 28 to return a partially or fully regenerated catalyst stream through the line 30 to second reaction zone 16 of the reactor 10. The volatile organic materials are removed from the stripper 24 through the line 32. Optionally, a catalyst cooler or heater (not shown) could be placed between regenerator 28 and the reactor 10 along line 30.

Alternatively, a captive bed of the same or other catalyst can be used to achieve the same outcome as that of the catalyst stripper 24 and the catalyst regenerator 28. This may allow the use of a different catalyst held at different reaction conditions to more efficiently carry out the second reactions in the second reaction zone 16 than can be achieved by the catalyst used in the first reaction zone 14.

In the oxygenate conversion reaction of the present invention, the temperature useful in both the first and second reaction zones varies over a wide range depending, at least in part, on the selected catalyst, the fraction of the regenerated catalyst in the catalyst mixture, and the reactor configuration. Although not limited to a particular temperature, best results are obtained if the process carried out in either reactor zone is conducted at a temperature from about 200° C. to about 700° C., desirably from about 250° C. to about 600° C., and most desirably from about 300° C. to about 500° C. Lower temperatures generally result in lower rates of reaction, and the formation rate of the desired light olefin products may become markedly slower. However, at higher temperatures, the process may not form an optimum amount of light olefin products, and the coking rate may become too high.

Light olefins form, although not necessarily in optimum amounts, at a wide range of pressures including, but not limited to, autogeneous pressures and pressures in the range of from about 0.1 kPa to about 5 MPa. A desired pressure in both the first and second reaction zones is from about 5 kPa to about 1 MPa and most desirably from about 20 kPa to about 500 kPa. The foregoing pressures do not include that of a diluent, if any, and refer to the partial pressure of the feedstock as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins will still form.

If desired, the reactions in the first or second reaction zones can be continued for a period of time sufficient to produce light olefins and/or to reach a steady state of production of light olefin products. It is also desirable to match the catalyst regeneration cycle and the conversion reactions to achieve the desired catalytic performance, such as activity maintenance, light olefin selectivity and control of $C_4^+$ by-products. In addition, a portion of the catalyst may be recirculated in the reactor before it is sent to the regenerator. Because at least some attrition occurs, a certain amount of replacement catalyst is used to replace the catalyst fines generated and separated.

A wide range of weight hourly space velocities (WHSV) for the feedstock, defined as weight feed per hour per weight of catalyst, function with the present invention. The WHSV should be high enough to maintain the catalyst in the fluidized state under the reaction conditions and within the reactor configuration and design. Generally, the WHSV is from about 1 hr to about 5000 hr$^{-1}$, desirably from about 2 hr$^{-1}$ to about 3000 hr$^{-1}$, and most desirably from about 5 hr$^{-1}$ to about 1500 hr$^{-1}$. For a feedstock comprising methanol, dimethyl ether, or mixtures thereof, the WHSV is most desirably in the range of from about 5 hr$^{-1}$ to about 300 hr$^{-1}$. Because the catalyst may contain other materials which act as inerts, fillers, or binders, the WHSV is calculated on the weight basis of oxygenates in the feedstock and the molecular sieve content of the catalyst.

In this invention, it is useful to define WHSV in the second reaction zone as the weight of products entering the second reaction zone divided by the weight of the catalyst contained in the second reaction zone. A separate first WHSV can be defined in terms of the rate of feed divided by the weight of catalyst present in the first reaction zone. The values of useful WHSVs used in the second reaction zone will be dependent upon the process conditions present, the activity of the catalyst present and the extend of extent of second reaction desired.

One or more diluents may be fed to the reactor with the oxygenates, such that the total feed mixture comprises diluent in a range of from about 1 mol % and about 99 mol %. Diluents also may be used in connection with recharging the at least partially regenerated catalyst back to the reactor. Diluents which may be employed in the process include, but are not necessarily limited to, water (steam), nitrogen, carbon dioxide, carbon monoxide, hydrogen, helium, argon, paraffins, light saturated hydrocarbons (such as methane, ethane, and propane), aromatic compounds, and mixtures thereof. Desired diluents are water (steam), nitrogen, and mixtures thereof.

The level of conversion of the oxygenates—particularly during a steady state of the reaction—can be maintained to reduce the level of unwanted by-products. Conversion can also be maintained sufficiently high to avoid the need for commercially unacceptable levels of recycling of unreacted feeds. A reduction in unwanted by-products is seen when conversion moves from 100 mol % to about 98 mol % or less. Recycling up to as much as about 50 mol % of the feedstock is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature, pressure, flow rate (i.e., space velocity); level and degree of catalyst regeneration; amount of catalyst re-circulation; the specific reactor configuration; the feed composition; and other parameters which affect the conversion.

Fixed beds may also be used to practice the process of the present invention, but are less desirable because an oxygenate-to-olefin conversion reaction run in such a reactor requires several stages with intercoolers or other heat removal devices because of the exothermicity of the reaction. Further, the oxygenate conversion reaction also results in a high pressure drop in a fixed bed due to the production of low pressure, low density gases. In addition, the processes of removing the deactivated catalyst and recharging the at least partially regenerated catalyst are difficult to perform.

Catalysts suitable for catalyzing the oxygenate-to-olefin conversion reaction of the present invention include molecular sieve catalysts. Molecular sieve catalysts can be zeolitic (zeolites) or non-zeolitic (non-zeolites). Useful catalysts may also be formed from mixtures of zeolitic and non-zeolitic molecular sieve catalysts. Desirably, the catalyst is a non-zeolitic molecular sieve. Desired catalysts for use with the process of the present invention include "small" and "medium" pore molecular sieve catalysts. "Small pore" molecular sieve catalysts are defined as catalysts with pores having a diameter of less than about 5.0 Angstroms. "Medium pore" molecular sieve catalysts are defined as catalysts with pores having a diameter in the range of from about 5.0 to about 10.0 Angstroms. Properly adjusted acid strength, acidity distribution, and acid site density are also keys to a good oxygenate conversion catalyst.

Useful zeolitic molecular sieve catalysts include, but are not limited to, mordenite, chabazite, erionite, ZSM-5, ZSM-34, ZSM-48 and mixtures thereof. Methods of making these catalysts are known in the art and need not be discussed here.

Silicoaluminophosphates ("SAPOs") are one group of non-zeolitic molecular sieve catalysts that are useful in the present invention. Processes for making useful SAPOs are known in the art. In particular, small pore SAPOs are desired. SAPO type molecular sieves have a three-dimensional microporous crystalline framework of $PO_2^+$, $AlO_2^-$, $SiO_2$ and $MeO_2^m$ tetrahedral units, with or without metals in the framework. The "m" superscript represents a net electric charge depending on the valence state of the substituent, Me. When "Me" has valence state of +2, +3, +4, +5, or +6 valence state, m is −2, −1, 0, +1, and +2, respectively. "Me" includes, but is not necessarily limited to, Zn, Mg, Mn, Co, Ni, Ga, Fe, Ti, Zr, Ge, Sn, Cr, and mixtures thereof. Because an aluminophosphate ($AlPO_4$) framework inherently is neutral in electrical charges, the incorporation of silicon or other metallic or nonmetallic elements into the framework by substitution generates more active catalytic sites, particularly acid sites, and increased acidity. Controlling the quantity and location of silicon atoms and other elements incorporated into an $AlPO_4$ framework is important in determining the catalytic properties of a particular SAPO-type molecular sieve. Suitable SAPOs for use in the invention include, but are not necessarily limited to, SAPO-34, SAPO-17, SAPO-18, SAPO-44, SAPO-56 and mixtures thereof. In a more desired embodiment, the SAPO is SAPO-34.

Substituted SAPOs form a class of molecular sieves known as "MeAPSOs," which are also useful in the present invention. Processes for making MeAPSOs are known in the art. SAPOs with substituents, such as MeAPSOs, also may be suitable for use in the present invention. Suitable substituents, "Me," include, but are not necessarily limited to, nickel, cobalt, manganese, zinc, titanium, strontium, magnesium, barium, and calcium. The substituents may be incorporated during synthesis of the MeAPSOs. Alternately, the substituents may be incorporated after synthesis of SAPOs or MeAPSOs using many methods. The methods include, but are not necessarily limited to ion-exchange, incipient wetness, dry mixing, wet mixing, mechanical mixing, and combinations thereof.

Desired MeAPSOs are small pore MeAPSOs having pore size smaller than about 5 Angstroms. Small pore MeAPSOs include, but are not necessarily limited to NiSAPO-34, CoSAPO-34, NiSAPO-17, CoSAPO-17, and mixtures thereof.

Aluminophosphates (ALPOs) with substituents, also known as "UMeAPOs," are another group of molecular sieves that may be suitable for use in the present invention, with desired MeAPOs being small pore MeAPOs. Processes for making MeAPOs are known in the art. Suitable substituents include, but are not necessarily limited to nickel, cobalt, manganese, zinc, titanium, strontium, magnesium, barium, and calcium. The substituents may be incorporated during synthesis of the MeAPOs. Alternately, the substituents may be incorporated after synthesis of ALPOs or MeAPOs using many methods. The methods include, but are not necessarily limited to ion-exchange, incipient wetness, dry mixing, wet mixing, mechanical mixing, and combinations thereof.

The catalyst may be incorporated into a solid composition, desirably solid particles, in which the catalyst is present in an amount effective to promote the desired conversion reaction. The solid particles may include a catalytically effective amount of the catalyst and matrix material, desirably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-aluminazirconias, and mixtures of these.

The solid particles desirably comprise about 1% to about 99%, more desirably about 5% to about 90% and still more desirably about 10% to about 80%, by weight of catalyst; and an amount of about 1% to about 99%, more desirably about 5% to about 90% and still more desirably about 10% to about 80%, by weight of matrix material.

The preparation of solid compositions, e.g., solid particles, comprising the catalyst and matrix material, is conventional and well known in the art and, therefore, is not discussed in detail here.

The present invention will be better understood with reference to the following examples, which illustrate, but are not intended to limit the present invention.

EXAMPLE 1

A 0.055 g sample of SAPO-34 catalyst that had previously been calcined in air at 550° C. for 16 hours was placed between two quartz wool plugs in a 4 mm diameter quartz reactor tube. The tube was then inserted into an electrically heated zone which was directly linked to a gas chromatograph for on-line analyses of products. The pressure inside of the reactor tube was maintained at 16.5 psig by using a back-pressure regulator. The temperature was maintained at 450±2° C. Helium was used as a carrier gas at a flow rate of 60 ml/min. One milliliter (ml) gas samples of ethylene ($C_2^=$) were injected successively at 30 minute intervals onto the catalyst. The products in the effluent were directed to a gas chromatographic column for analyses. The ethylene conversion was calculated by subtracting from 100% all of the detected gas phase hydrocarbon products other than ethylene feed itself. Selectivities to the products of interest are shown in Table I. Coke yield was not determined.

EXAMPLE 2

The procedure described in EXAMPLE 1 was repeated except that one milliliter (ml) gas samples of propylene ($C_3^=$) were used as feed. The propylene conversion was calculated by subtracting from 100% all of the detected gas phase hydrocarbon products other than propylene feed itself. Selectivities to the products of interest are shown in Table I. Coke yield was not determined.

EXAMPLE 3

The procedure described in EXAMPLE 1 was repeated except that one milliliter (ml) gas samples of 1-butene (1-n-$C_4^=$) were used as feed. The butene-1 conversion was calculated by subtracting from 100% all of the detected gas phase hydrocarbon products other than butene-1 feed and other butene isomers. Selectivities to the products of interest are shown in Table I. Coke yield was not determined.

EXAMPLE 4

The procedure described in EXAMPLE 1 was repeated except that one microliter ($\mu$l) liquid samples of 1-pentene (1-n-$C_5^=$) were used as feed. The pentene-1 conversion was calculated by subtracting from 100% all of the detected gas phase hydrocarbon products other than butene-1 feed and other C5+ compounds. Selectivities to the products of interest are shown in Table I. Coke selectivity was not determined in this example.

EXAMPLE 5

The procedure described in EXAMPLE 1 was repeated except that one microliter ($\mu$l) liquid samples of 1-heptene (1-n-$C_7^=$) were used as The heptene-1 conversion was calculated by subtracting from 100% all of the detected gas phase hydrocarbon products other than heptene-1 feed and other C5+ compounds. Selectivities to the products of interest are shown in Table I. Coke selectivity was not determined in this example.

EXAMPLE 6

The procedure described in EXAMPLE 3 was repeated except that the reaction temperature was maintained at 500° C. The butene conversion was calculated by subtracting from 100% all of the detected gas phase hydrocarbon products other than butene-1 feed itself and other butene isomers. Selectivities to the products of interest are shown in Table I. Coke selectivity was not determined in this example.

TABLE I

| Example | Feed | Conversion (%) | Selectivity (%) | | | | Relative Rxn Rate* |
| | | | $C_2^=$ | $C_3^=$ | $C_4^=$ | $C_5^{=+}$ | |
| --- | --- | --- | --- | --- | --- | --- | --- |
| 1 | $C_2^=$ | 2.2 | N.A. | 55.3 | 14.7 | 6.6 | 1 |
| 2 | $C_3^=$ | 22.8 | 15.3 | N.A. | 56.6 | 11.8 | 12 |
| 3 | 1-n-$C_4^=$ | 31.5 | 9.8 | 66.0 | N.A. | 13.8 | 17 |

TABLE I-continued

| Example | Feed | Conversion (%) | Selectivity (%) | | | | Relative Rxn Rate* |
| --- | --- | --- | --- | --- | --- | --- | --- |
| | | | $C_2^=$ | $C_3^=$ | $C_4^=$ | $C_5^{=+}$ | |
| 4 | 1-n-$C_5^=$ | 13.3 | 11.4 | 45.2 | 41.1 | N.A. | 6 |
| 5 | 1-n-$C_7^=$ | 52.6 | 1.4 | 47.0 | 51.0 | N.A. | 33 |
| 6 | 1-n-$C_4^=$ @ 500° C. | 45.7 | 15.8 | 66.3 | N.A. | 15.5 | 27 |

*The reaction rates were calculated based on first order reaction rates and weight hourly space velocities (WHSV) were estimated. The rates are expressed as relative rates to the ethylene reaction rate, which is set as 1, in order to mitigate any potential WHSV measurement inaccuracies.

The results in Table I show that ethylene is relatively unreactive under typical oxygenate conversion conditions. The relative reaction rates of converting $C_3^=$ to $C_7^=$ were at least six times faster than the rate of converting ethylene. Accordingly, longer chain olefins are preferentially converted to shorter chain olefins when contacting a non-zeolitic molecular sieve catalyst such as SAPO-34. When a regenerated catalyst is sent back to the reactor, it is advantageous to expose the regenerated catalyst to the oxygenate conversion products first to further convert heavier olefins to ethylene and/or propylene. This method, in effect, increases the overall yield or selectivity of the desired light olefins and reduces the amount of heavier olefins.

Example 6 shows a much higher reaction rate of converting butenes to light olefins by contacting with an oxygenate conversion catalyst at a higher temperature without adversely affecting the selectivities to ethylene and propylene.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting at least a portion of the light olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins produced by the process of the present invention or olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore are not discussed here.

As stated above, the preferred oxygenate for use in the methods of the present invention is methanol. Each of the methods of the present invention may also include the step of forming methanol. Methods for forming oxygenates, such as methanol, are known in the art and will not be discussed in detail here. Two methods for forming oxygenates include fermentation and formation from synthesis gas. These methods are also useful to form other oxygenates.

As also stated above, the at least partially regenerated catalyst can be used to manage heat within the conversion reactor. As one skilled in the art will appreciate, the conversion of the oxygenate feedstock to light olefins is an exothermal reaction. By returning the at least partially regenerated catalyst to contact the by-products of the conversion reaction, the longer chain by-products of the conversion reaction are converted to shorter chain light olefin products. The conversion of the longer chain by-products to shorter chain light olefin products is an endothermic reaction. The conversion of the by-products into light olefin products consumes heat produced by the conversion of the oxygenate feed, thus, reducing the overall heat of reaction in a reactor during a catalyzed chemical conversion process. By feeding the hot catalyst to the reactor, a catalyst cooler may be eliminated from the apparatus used to produce the desired olefins or, at least, the catalyst cooler can be reduced in size and/or cooling duty. The hot catalyst is cooled in the reactor by the endothermic conversion of the longer chain ($C_4$, $C_5$, $C_6$ and longer) olefins into ethylene, propylene and coke.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

What is claimed is:

1. A method for converting an oxygenate feedstock to an olefin product comprising:

contacting an oxygenate feedstock with silicoaluminophosphate catalysts in a first reaction zone of a reactor system under conditions effective to produce a first olefin product stream comprising light olefins and $C_4^+$ olefins;

directing at least a portion of the catalysts from the first reaction zone and the first olefin product stream to a second reaction zone;

directing at least a portion of the catalysts in the second reaction zone to a regenerator;

regenerating the at least a portion of the catalysts in the regenerator to form regenerated catalysts;

directing the regenerated catalysts from the regenerator to the second reaction zone; and contacting the first olefin product stream with at least a portion of the regenerated catalysts in the second reaction zone of the reactor system wherein $C_4^+$ olefins are converted to light olefins, thereby producing a final olefin product.

2. The method of claim 1, wherein the reactor system is a riser reactor.

3. The method of claim 2, wherein the olefin product stream from the first reaction zone comprises at least 50 wt. % light olefin.

4. The method of claim 3, wherein the olefin product stream from the first reaction zone comprises at least 55 wt. % light olefin.

5. The method of claim 4, wherein the olefin product stream from the first reaction zone comprises at least 60 wt. % light olefin.

6. The method of claim 2, wherein the oxygenate feedstock comprises at least 50 wt. % oxygenate.

7. The method of claim 2, wherein the olefin product stream from the first reaction zone comprises less than 50 wt. % $C_4^+$ hydrocarbons.

8. The method of claim 7, wherein the olefin product stream from the first reaction zone comprises less than 40 wt. % $C_4^+$ hydrocarbons.

9. The method of claim 8, wherein the olefin product stream from the first reaction zone comprises less than 30 wt. % $C_4^+$ hydrocarbons.

10. The method of claim 2, wherein the catalysts directed to the second reaction zone have a coke content of less than 5 wt. %.

11. The method of claim 10, wherein the catalysts directed to the second reaction zone have a coke content of less than 2 wt. %.

12. The method of claim 11, wherein the catalysts directed to the second reaction zone have a coke content of less than 1.0 wt. %.

13. The method of claim 2, further comprising separating light olefins from the final olefin stream.

14. The method of claim 13, further comprising contacting at least a portion of the light olefin with a polyolefin-forming catalyst under conditions effective to form a polyolefin.

15. The method of claim 1, further comprising:

circulating at least a portion of the catalysts from the second reaction zone to the first reaction zone.

16. The method of claim 1, wherein the first and second reaction zones are in separate reactors.

17. The method of claim 1, wherein the first and second reaction zones are in the same reactor.

18. The method of claim 1, wherein the contacting occurs in a fluidized bed reactor including a riser region, and the second reaction zone is located at a point above the riser region.

* * * * *